US007489785B2

(12) United States Patent
Donaldson et al.

(10) Patent No.: US 7,489,785 B2
(45) Date of Patent: Feb. 10, 2009

(54) NOISE CANCELLATION SYSTEM AND HEADPHONE THEREFOR

(76) Inventors: Mark Donaldson, 20 Cowie St., Parnell, Auckland (NZ); Graeme Colin Fuller, Unit 1, 82 Banks Road, Mt. Wellington, Auckland 1001 (NZ)

( * ) Notice: Subject to any disclaimer, the term of this patent is extended or adjusted under 35 U.S.C. 154(b) by 134 days.

(21) Appl. No.: 10/520,036

(22) PCT Filed: Jun. 26, 2003

(86) PCT No.: PCT/NZ03/00134

§ 371 (c)(1), (2), (4) Date: Dec. 28, 2004

(87) PCT Pub. No.: WO2004/002383

PCT Pub. Date: Jan. 8, 2004

(65) Prior Publication Data

US 2005/0213773 A1 Sep. 29, 2005

(30) Foreign Application Priority Data

Jun. 28, 2002 (NZ) ..................................... 519863

(51) Int. Cl.
*A61F 11/06* (2006.01)
*G10K 11/16* (2006.01)
*H03B 29/00* (2006.01)

(52) U.S. Cl. ....................................... 381/71.6; 381/72

(58) Field of Classification Search ..... 381/71.1–71.14, 381/74, 72, 73.1
See application file for complete search history.

(56) References Cited

U.S. PATENT DOCUMENTS

| | | | | |
|---|---|---|---|---|
| 5,815,582 | A | 9/1998 | Claybaugh et al. | |
| 6,061,456 | A * | 5/2000 | Andrea et al. | 381/71.6 |
| 6,278,786 | B1 * | 8/2001 | McIntosh | 381/71.6 |
| 2001/0050993 | A1 * | 12/2001 | Douglas | 381/71.6 |
| 2003/0002643 | A1 | 1/2003 | Siebel et al. | |

FOREIGN PATENT DOCUMENTS

| | | |
|---|---|---|
| WO | WO 93/25167 | 12/1993 |
| WO | WO 93/26084 | 12/1993 |
| WO | WO 99/05998 | 2/1999 |
| WO | WO 01/06812 | 1/2001 |
| WO | WO 01/67433 | 9/2001 |
| WO | WO 02/082422 | 10/2002 |
| WO | WO 03/030145 | 4/2003 |
| WO | WO 03/030146 | 4/2003 |

* cited by examiner

*Primary Examiner*—Xu Mei
(74) *Attorney, Agent, or Firm*—Brouse McDowell; John M. Skeriotis

(57) ABSTRACT

A noise cancellation system includes a headphone having a sound transducer and a headphone speaker. Noise cancellation circuitry is provided remote from the headphone and supplies the headphone speaker and is supplied from the sound transducer. A filter normalizes the output from the sound transducer of the headphone to the noise cancellation circuitry.

7 Claims, 2 Drawing Sheets

NOISE CANCELLATION SYSTEM AND HEADPHONE THEREFOR

This application claims priority from PCT/NZ2003/000134, entitled NOISE CANCELLATION SYSTEM AND HEADPHONE THEREFOR, filed Jun. 26, 2003, which claims priority from New Zealand Patent No. 519,863, entitled NOISE CANCELLATION SYSTEM AND HEADPHONE THEREFOR, filed Jun. 28, 2002, both of which are incorporated herein by reference.

I. BACKGROUND OF THE INVENTION

A. Field of Invention

This invention relates to noise cancellation systems, and is directed particularly, but not solely, towards a headphone noise cancellation system.

B. Description of the Related Art

It is known to provide noise compensation systems with either noise cancellation built into the headphone or with a fixed noise cancellation system forming part of the system into which a headphone is plugged. U.S. Pat. No. 5,182,774 exemplifies the former type which have the noise cancellation tailored to each headphone type. The latter have previously been designed for use with only one manufacture of headphone and the noise cancellation is problematic with other types because of variations in frequency response and impedance which render the cancellation ineffective and can, at worst, result in positive feedback and instability.

II. SUMMARY OF THE INVENTION

According to one aspect of this invention, a noise cancellation system includes: a headphone including a sound transducer and a headphone speaker; noise cancellation circuitry provided remote from the headphone, supplying the headphone speaker, and being supplied from the sound transducer; and, a filter to normalize the output from the sound transducer of the headphone to the noise cancellation circuitry.

According to another aspect of this invention, the filter may be located at the output of the sound transducer to enable effective noise cancellation to be achieved in use.

According to another aspect of this invention, the filter may comprise a passive electronic filter.

According to still another aspect of this invention, the filter may comprise a resistor/capacitor network.

According to another aspect of this invention, the filter may be a high pass filter in parallel with the sound transducer.

According to another aspect of this invention, the sound transducer may comprise an electret condenser microphone.

According to yet another aspect of this invention, a headphone for a noise cancellation system includes: one or more headphone speakers for providing sound to a user; at least one sound transducer provided in the headset adjacent to the speaker; wherein the output of the sound transducer is provided as an electrical signal and is provided to a filter; and, wherein the output of the filter is available to noise cancellation circuitry to cancel noise from the signal being delivered to the speaker.

It is one object of the present invention to provide an improved noise cancellation system.

It is another object of the present invention to provide an improved headset for a noise cancellation system.

It is yet another object of the present invention to provide the public with a useful choice.

Various benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, a preferred embodiment of which will be described in detail in this specification and illustrated in the accompanying drawings which form a part hereof and wherein.

IV. DESCRIPTION OF THE PREFERRED EMBODIMENT

In general terms, the invention provides a way of allowing noise cancellation circuitry which is typically provided remote from a headphone, to be able to provide effective noise cancellation for a number of different headphone designs. This is achieved by providing the noise cancellation headphone sound transducer (typically a microphone such as an electret condenser microphone) with a passive filter so that the feedback signal provided by the microphone is appropriately conditioned for a "generic" active noise cancellation circuit or normalized. Therefore, the invention allows the noise cancellation circuitry to be designed to be operative over a certain phase range of input feedback signals from a headset. This in turn means that a filter placed on the headset feedback signal may be appropriately configured for each different sort of headset so as to be acceptable to the noise cancellation circuitry and enable collective noise cancellation to be achieved.

The most preferred form of the invention the filter comprises a simple passive filter. Most preferably it is a resistor/capacitor filter as described further below. We have found that simple resistor capacitor passive filter provides an appropriate transfer function that is suitable for active noise cancellation applications. This simple passive filter may have the values of resistance or capacitance varied dependent upon the nature of the headphone, the headphone sound transducer etc.

Figure 1:
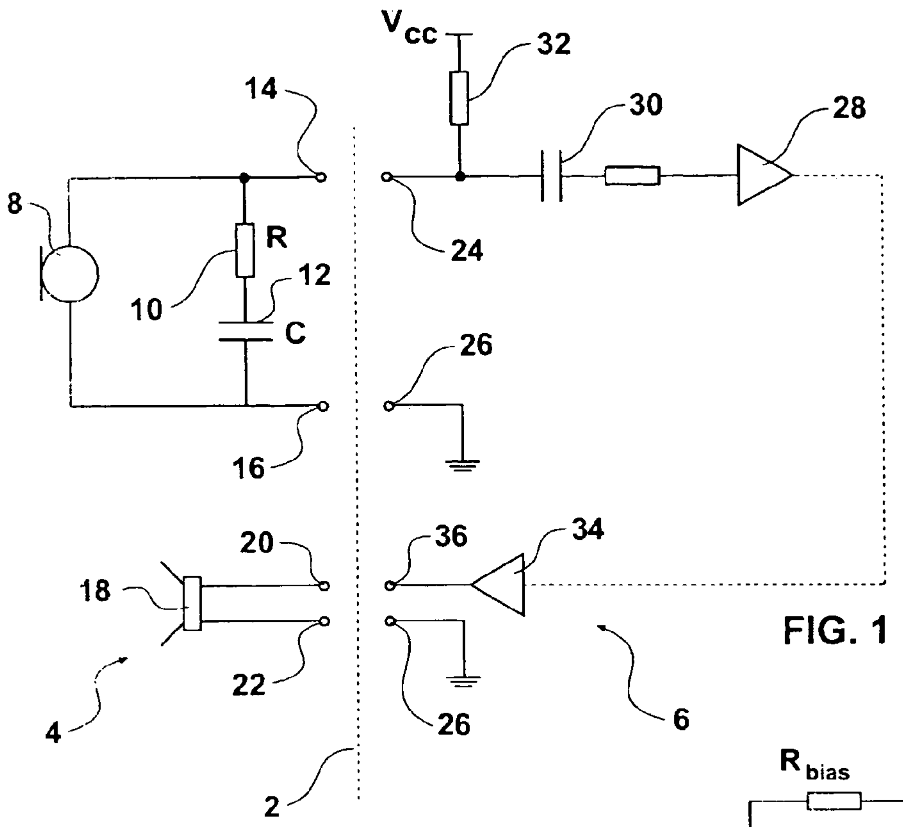
FIG. 1 is a circuit schematic of a noise cancellation system according to the invention.

Turning now to FIG. 1, a schematic of an implementation of the invention as shown. The headphone is shown to the left of dashed line 2 in the figure and is generally indicated by arrow 4. On the other side of the drawing, i.e., to the right hand side of dashed line 2, the noise cancellation circuitry is shown generally referenced 6. By way of example, the noise cancellation circuitry may be provided in a portable electronic device such as a portable audio system including those sold under the trade mark WALKMAN. The circuitry could alternatively be provided in a home stereo system, television set or a variety of other devices which provide sound to a user. However, more typically, the noise cancellation circuitry 6 will be provided in a passenger vehicle. Again, a number of different forms of passenger transport may be provided so the noise cancellation circuitry may be provided in a seat installation (possibly an arm rest area) of a commercial aeroplane, a train a bus, a private automobile, or the like.

In FIG. 1, the sound transducer for the headphone 4 is an electret condenser microphone 8, and the output of the microphone is provided to a passive filter network comprising resistor 10 and capacitor 12. The output from the passive filter network is referenced 14 and 16, and these outputs are typically provided as pins on a plug which is acceptable to an appropriate jack or socket on the device that includes the noise cancellation circuitry.

Still referring to FIG. 1, the headset 4 also includes a speaker 18 which has input signal connections 20 and 22. Again, connections 20 and 22 are in use electrically connected to an appropriate plug pins (not shown) so that they can be supplied with an appropriate electrical signal from the output of the noise cancellation circuitry that is provided in the corresponding socket remote from the headphone.

Turning now to the noise cancellation circuitry, the input to the noise cancellation circuitry from the microphone is represented by inputs 24 and 26. Input 26 may be a reference such as ground, input 24 is provided to an amplifier 28 via capacitor 30. The power supply VCC and bias resistor 32 are also provided. The output of amplifier 28 is fed to noise cancellation circuitry which may comprise a passive network or be active, for example being implemented using a microprocessor. Noise cancellation circuitry which may be used is not described in this document, as it is known to those skilled in the art. The output from the noise cancellation circuitry is provided to an appropriate output amplifier 34 to be provided to output terminals 36 and 26 which connect to terminals 2 and 22 for the headphone speaker.

Figure 2:
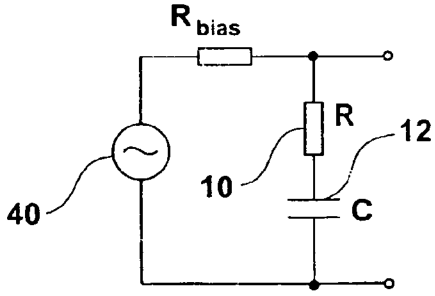
FIG. 2 is a schematic of an equivalent circuit for a headset microphone and filter according to the invention.

Turning now to FIG. 2, further explanation of the passive filter network described above is illustrated. The sound transducer 8 in the preferred form of the invention comprises an electret condenser microphone. This microphone behaves as a current source from a signal viewpoint. Using a Norton to Thevenin conversion the microphone signal can be represented as a voltage source in series with the bias resistor, Rbias. In FIG. 2, the microphone signal is represented as voltage source 40, the output of which is in series with a bias resistor Rbias. The voltage source and bias resistor are in parallel with the passive filter comprising resistor 10 and capacitor 12. The network shown in FIG. 2 provides a transfer function which is:

$$\frac{1 + sRC}{1 + s(R + R_{bias})C}$$

This is a suitable transfer function for active noise cancellation applications, i.e., the output from the circuit shown in FIG. 2 is appropriate for provision to a "generic" active noise cancellation circuit. Therefore, it can be seen that the values of resistance and capacitance of components 10 and 12 of FIG. 2 may be chosen dependent upon the general acoustic properties of the headphone e.g., shape and size of the ear piece and orientation of the microphone relative to the speaker.

Figure 3:
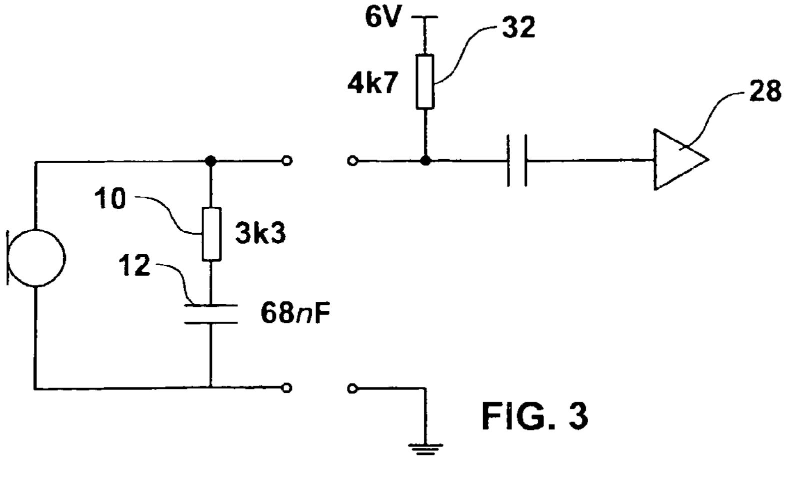
FIG. 3 is a schematic illustrating one example of a practical implementation of the invention.
Figure 4:
FIG. 4 is a perspective view of a set of headphones.

Finally, in FIG. 3, a typically implementation is illustrated. The reference numerals used in this figure are the same as those used with reference to FIG. 1 and it can be seen that resistor 10 has value of 3.3 kΩ, capacitor 12 is 68 nanofarads, and the bias resistor 32 is 4.7 kΩ. Typically the headphone compensation is determined by targeting the noise cancellation at the best headphone to be catered for and then compensating other headphones to bring them to the same performance level.

From the foregoing, we see that the invention provides significant advantages in that a number of different headphones or headsets may be used to provide noise cancellation without having to redesign, alter or modify noise cancellation circuitry for which they are used. Therefore, noise cancellation circuitry may be designed to standard parameters and embodied in various devices such as personal stereos or passenger seat installations while allowing users to use their own preferred headset, or a variety of different headsets.

The preferred embodiments have been described, hereinabove. It will be apparent to those skilled in the art that the above methods may incorporate changes and modifications without departing from the general scope of this invention. It is intended to include all such modifications and alterations in so far as they come within the scope of the appended claims or the equivalents thereof.

Having thus described the invention, it is now claimed.

We claim:

1. A noise cancellation system comprising:

a noise cancellation circuit having a noise cancellation input to receive a noise cancellation input signal required for effecting noise cancellation, and a noise cancellation output for providing an output signal processed to cancel noise dependent on the noise cancellation input signal, the noise cancellation circuit being operative over a predetermined phase range of noise cancellation input signal supplied to the noise cancellation input;

a plurality of headphones provided remote from the noise cancellation circuit, each headphone having a headphone speaker and a sound transducer, at least one headphone of the plurality of headphones having a different acoustic property from the other headphone(s) such that the sound transducer does not provide a noise cancellation input signal within the predetermined phase range, and the at least one headphone having a passive filter provided to filter the output of the sound transducer, and each headphone being individually electrically connectable to the noise cancellation circuit so that the output of the passive filter or the output of the sound transducer is provided to the noise cancellation input and the noise cancellation output signal is provided to the headphone speaker; and, wherein the passive filter for the at least one headphone is configured to modify the output of the sound transducer to provide a noise cancellation input signal which is within the predetermined phase range.

2. A noise cancellation system as claimed in claim 1 wherein the filter is located at the output of the sound transducer to enable effective noise cancellation to be achieved in use.

3. A noise cancellation system filter as claimed in claim 2 wherein the filter comprises a passive electronic filter.

4. A noise cancellation system filter as claimed in claim 3 wherein the filter comprises a resistor/capacitor network.

5. A noise cancellation system filter as claimed in claim 1 wherein the filter is a high pass filter in parallel with the sound transducer.

6. A noise cancellation system as claimed in claim 1 wherein the sound transducer comprises an electret condenser microphone.

7. The noise cancellation system as claimed in claim 1 wherein the noise cancellation circuit comprises a microprocessor.

* * * * *